United States Patent
Scholten et al.

(10) Patent No.: US 9,746,551 B2
(45) Date of Patent: Aug. 29, 2017

(54) MULTI-APPLICATION-TRANSCEIVER DEVICE AND METHODS FOR TARGET MONITORING

(71) Applicants: Ulrich Scholten, Mougins (FR); Eric Moskwa, Iserlohn (DE)

(72) Inventors: Ulrich Scholten, Mougins (FR); Eric Moskwa, Iserlohn (DE)

( * ) Notice: Subject to any disclaimer, the term of this patent is extended or adjusted under 35 U.S.C. 154(b) by 0 days.

(21) Appl. No.: 14/276,380

(22) Filed: May 13, 2014

(65) Prior Publication Data
US 2015/0276925 A1  Oct. 1, 2015

(30) Foreign Application Priority Data
Mar. 25, 2014  (EP) .................................... 14161623

(51) Int. Cl.
*G01S 13/66* (2006.01)
*A61B 5/00* (2006.01)
(Continued)

(52) U.S. Cl.
CPC ............ *G01S 13/66* (2013.01); *A61B 5/0002* (2013.01); *A61B 5/0507* (2013.01); *A61B 5/1102* (2013.01); *A61B 5/117* (2013.01); *G01S 7/003* (2013.01); *G01S 13/02* (2013.01); *G01S 15/02* (2013.01); *G01S 17/02* (2013.01); *A61B 5/113* (2013.01); *A61B 5/1113* (2013.01);
(Continued)

(58) Field of Classification Search
CPC . A61B 5/015; A61B 2562/164; A61B 5/0002; A61B 5/0507; A61B 5/4094
USPC .......................................... 702/150; 600/300
See application file for complete search history.

(56) References Cited

U.S. PATENT DOCUMENTS

| | | | |
|---|---|---|---|
| 6,325,759 B1 * | 12/2001 | Pelissier | 600/443 |
| 6,335,625 B1 * | 1/2002 | Bryant et al. | 324/637 |

(Continued)

FOREIGN PATENT DOCUMENTS

GB    2349759 A    11/2000

*Primary Examiner* — Mohamed Charioui
(74) *Attorney, Agent, or Firm* — Brake Hughes Bellermann LLP (57) ABSTRACT

A multi-application-transceiver device, control computer, computer implemented method and computer program product for operating the multi-application-transceiver device is disclosed. At least one signal transceiver receives a reflected signal in response to an original signal sent by the at least one signal transceiver. The reflected signal is reflected from at least one target object. A signal conversion unit converts the reflected signal into digital format. A digital signal processor component pre-processes the converted reflected signal using an alterable rule engine with a received rule set to discriminate a state inn change of the at least one target object against an earlier state of the at least one target object in the context of a particular monitoring application. A middleware component communicates with at least one remote computing device wherein communicate includes to send the pre-processed signal to the remote computing device, and to receive from the at least one remote computing device the rule set for the alterable rule engine. The received rule set defines an application specific setting for the at least one signal transceiver and for the digital signal processor component to enable the particular monitoring application.

16 Claims, 6 Drawing Sheets

(51) Int. Cl.

| | | |
|---|---|---|
| *G01S 17/02* | (2006.01) | |
| *G01S 7/00* | (2006.01) | |
| *G01S 13/02* | (2006.01) | |
| *G01S 15/02* | (2006.01) | |
| *A61B 5/05* | (2006.01) | |
| *A61B 5/117* | (2016.01) | |
| *A61B 5/11* | (2006.01) | |
| *A61B 5/113* | (2006.01) | |

(52) U.S. Cl.
CPC ............. *A61B 5/1116* (2013.01); *A61B 5/444* (2013.01); *A61B 5/4818* (2013.01)

(56) References Cited

U.S. PATENT DOCUMENTS

| | | | |
|---|---|---|---|
| 7,428,468 B2* | 9/2008 | Takemura et al. | 702/159 |
| 8,319,678 B2* | 11/2012 | Weiss | 342/22 |
| 2002/0050932 A1* | 5/2002 | Rhoades et al. | 340/870.16 |
| 2005/0119532 A1* | 6/2005 | Cloutier | 600/300 |
| 2007/0293781 A1* | 12/2007 | Sims | A61B 5/1135 600/534 |
| 2010/0245091 A1* | 9/2010 | Singh et al. | 340/573.1 |
| 2011/0060215 A1* | 3/2011 | Tupin, Jr. | A61B 5/0507 600/425 |
| 2013/0053653 A1 | 2/2013 | Cuddihy et al. | |
| 2013/0245436 A1* | 9/2013 | Tupin, Jr. | A61B 5/0444 600/430 |

* cited by examiner

MULTI-APPLICATION-TRANSCEIVER DEVICE AND METHODS FOR TARGET MONITORING

CROSS REFERENCE TO RELATED APPLICATIONS

This application claims priority under 35 U.S.C. §119 to European Patent Application No. 14161623, filed Mar. 25, 2014, titled "APPLICATION AGNOSTIC SENSOR, CONTROL COMPUTER AND METHODS FOR OPERATING" which is incorporated herein by reference in its entirety.

TECHNICAL FIELD

The present invention generally relates to electronic data processing, and more particularly, relates to methods, computer program products and systems for sensing and processing reflected signals.

BACKGROUND

In the prior art application specific radar sensors are known for remotely monitoring the health condition of human beings. For example, patent application GB2349759 discloses a device for monitoring a heartbeat comprising a radar adapted to detect a beam of microwave radiation towards a living body whose heartbeat is to be monitored, and to derive a phase-shift signal representative of the phase-shift between a transmitted signal and a reflected signal, a controllable filter to filter the phase-shift signal and to pass a frequency spectrum anticipated to contain signals corresponding to the heartbeat to be monitored, an output of the filter being passed to a spectral analysis unit to conduct a spectral analysis to isolate the signals representative of the heartbeat, the spectral analysis unit being adapted to control the filter by reducing the pass-band width of the filter and selecting the pass-band frequency range so that the filter passes the signals corresponding to the heartbeat, the arrangement providing an output signal representative of the heartbeat being monitored.
Preferably the phase-shift signal is passed through analogue-to-digital converter, and the filter is a digital filter. The output signal representative of the heartbeat can be monitored and an alarm signal may be generated if the monitored signal meets predetermined criteria.
The alarm is associated with additional sensor means adapted to sense a parameter indicative of the approach of sleep to the person whose heartbeat is being monitored. The radar incorporates an antenna, the antenna being located in part of a support for the body whose heartbeat is to be monitored to direct said beam of microwave radiation towards the body supported by the support.

Patent application US2013053653 discloses a system for non-contact monitoring of a subject. The system includes one or more range-controlled radars configured to transmit a radar signal and receive a reflected radar signal from the subject in a resting state. Further, the system also includes at least one processing unit communicatively coupled to the one or more range-controlled radars. The processing unit is configured to non-invasively detect one or more motion and/or physiological parameters corresponding to the subject using the one or more range-controlled radars. The motion parameters comprise one or more activity levels and the physiological parameters comprise one or more of heartbeat and respiration. The processing unit determines one or more patterns in the motion parameters detected over a designated motion period of time. Additionally, the processing unit determines one or more patterns in the physiological parameters detected over the designated physiological period of time. The processing unit then assesses a health condition of the subject based on the determined patterns of the motion parameters and/or the determined patterns of the physiological parameters. The system further includes a data repository coupled to the processing unit to store one or more of the reflected radar signal data, the motion parameters, the physiological parameters and/or the determined patterns.

The prior art sensors are limited to a specific application based on a predefined sensor type and are inflexible with regards to multi-application use scenarios for said sensors. Further such sensors have powerful on-board computing resources to locally perform the data processing according to the application logic. Such complex data processing is typically associated with increased energy consumption of the devices.

SUMMARY

Therefore, there is a need to improve reflection signal based sensors for remote monitoring in that the sensors are enabled for multi-application use while at the same time reducing hardware requirements and energy consumption of the sensors without sacrificing the quality of the data processing, that is, the analysis of the sensed data.

The above technical problem is solved by embodiments of the invention as disclosed in the independent claims.

In one embodiment, a multi-application-transceiver device includes at least one signal transceiver configured to receive a reflected signal in response to an original signal sent by the at least one signal transceiver. The reflected signal is reflected from at least one target object. For example, the at least one target may be a person or a group of persons which is located within the detection range of the at least one signal transceiver (e.g., within a room where the multi-application transceiver device is mounted). The at least one signal transceiver can include one or more imaging sensors selected from the group of radar sensor, sonar sensor, LIDAR sensor and infrared sensor. A radar transceiver, as used hereinafter, stands for a device operating in a frequency range starting at 1 GHz. There is no upper limitation to the electromagnetic frequency. That is, frequencies in the Terra-Hertz range are explicitly included. Using a combination of various sensor types allows integrating data of different types (e.g., transverse and longitudinal waves) provided by the various sensors which may enhance the reliability of information that is retrieved about the at least one target object based on the reflected signals. In one embodiment, the multi-application-transceiver device may use radar and/or sonar imaging sensors operating in a low power range which are suitable for a constant monitoring of human beings but also for close range perimeter surveillance and analysis. Imaging sensor, as used herein after, stands for sensors which are traditionally part of imaging processes generating an "artifact that depicts or records visual perception, for example a two-dimensional picture that has a similar appearance to some subject—usually a physical object or a person, thus providing a depiction of it". The provision of imaging sensors in pursuit of protecting the privacy of the imaged persons may renounce to use optical cameras that produce close-to-reality images, and not to use microphones which are able to track human voice. In the context of an integrated design, e.g., in smartphones, microphones and cameras are generally included.

The multi-application-transceiver device further includes a signal conversion unit configured to convert the reflected signal(s) into digital format. The converted signal(s) are then pre-processed by a digital signal processor component (DSP) of the multi-application-transceiver device. The DSP uses an alterable rule engine for pre-processing the converted reflected signal using. The alterable rule engine can be configured with application specific rule sets which are received from one or more remote computing devices. A received rule set is used by the DSP to discriminate a change in state of the at least one target object against an earlier state of the at least one target object in the context of a particular monitoring application.

In one embodiment, the state in change of the at least one target object may be caused by a dislocation of the at least one target object. In other words, the particular monitoring application when executed by the DSP may be able to discriminate a movement of the at least one target object against a static environment around the at least one target object. Such a movement may include the movement of a person's body surface which is caused by the person's heartbeat or breathe. In one embodiment, the state in change of the at least one target object may be caused by a cross-section change of the at least one target object. For example, a baby may turn its head upside down while sleeping. The change of the measured cross-section of the baby's head may then change from "nose up" to "nose down". In another example, the size of a melanoma under the person's (target object) skin may change which can be measured by determining multiple cross-section states over time. In one embodiment, the change in state may be caused by the original signal stimulating the target object (e.g., a sample). As a result, the target object is transformed into an excited state and the reflected signal may include frequencies (e.g., resonance frequencies) which are characteristic for change in state of the monitored target object.

The communication with the one or more remote computing devices is established by a middleware component. Through the middleware component the multi-application-transceiver device can receive the rule set for the alterable rule engine. The received rule set defines an application specific setting for the at least one signal transceiver and for the DSP component to enable the particular monitoring application. Further, the middleware component can send the pre-processed signal to the one or more remote computing devices (e.g., for further analysis or evaluation). Thereby, the pre-processed signal may include at least information with respect to the discriminated change in state (e.g., movement, change in size, change in frequency, etc.), In one embodiment, the multi-application-transceiver device can be used to perform a particular health monitoring application by monitoring one or more parameters indicating a health status of the at least one target object. The detailed description provides descriptions of two example health monitoring application—health supervision of babies and melanoma detection.

In one embodiment, the multi-application-transceiver device has at least one signal transceiver equipped with one or more phased array antennae and/or probes. The one or more phased array antennae and/or probes may be configured to be controlled independently and concurrently. A signal transceiver which is equipped with two or more phased array antennae or probes that can be controlled independently and concurrently can provide sensor measurement data to produce high resolution images of the analyzed target object. Even three dimensional images can be generated on the basis of such sensor data which allow, for example, detecting if a baby lies on its back or front. In other words, the system can be sensitive enough to detect whether the nose of the baby is free or pressed on a pillow.

In one embodiment, the particular monitoring application of the multi-application-transceiver device is configured to discover and track a plurality of target objects within the range of the at least one signal transceiver. That is, the application supports multi-target tracking which allows together with a moving target indication method to identify multiple targets. For example, the monitoring application can distinguish between three persons in the same room and find out which persons are the parents and which one is the baby. For example, the system can identify an individual person due to its specific biometric heart pattern by applying this pattern when, for example, several individuals are monitored.

In one embodiment, the multi-application-transceiver device may receive additional sensor data from at least one non-imaging sensor. Such additional sensor data can be used for computing the pre-processed signal and improve the quality (e.g., improved accuracy) of the pre-processed signal data for further processing by the one or more remote computers.

In one embodiment, the multi-application-transceiver can control an actuator which is either communicatively coupled or integrated with the multi-application-transceiver device. The received rule set may be configured to cause the actuator to indicate a device and/or application status if a certain condition is met. For example, if a baby stops breathing the digital signal will show a characteristic behavior reflecting the situation and a corresponding emergency rule may immediately trigger an alarm actuator (e.g., a hooter) to alarm the baby and thus potentially save the baby's life.

In one embodiment, the particular monitoring application may be configured to discover a presence of a particular macromolecule in the one or more target objects and to estimate the concentration of the particular macromolecule in the one or more target objects through the magnitude of re-emitted electromagnetic radiation having a frequency within the resonance frequency range of the particular macromolecule. It is to be noted that the term reflected signal, as used throughout this document, also includes signals being re-emitted by the target object(s) in response to the original signal. That is, any radiation which is re-emitted by the target object as a signal which is stimulated or induced by the original signal is considered to be a reflected signal within the context of this document. In this embodiment discriminating a change in the state of a target object includes the detection of a frequency in the reflected signal which results from the transition of the target object into an excited energetic state. The detection and analysis is then based on the magnitude of re-emission of the resonance frequency.

In one embodiment, the middleware component can receive a further rule set for the alterable rule engine from the at least one remote computing device, This further received rule set may define a further application specific setting for the at least one signal transceiver and for the digital signal processor component to enable a further monitoring application. The digital signal processor component can then pre-process the converted reflected signal in the context of the particular monitoring application and the further monitoring application in parallel. In other words, the multi-application-transceiver device can operate several applications at the same time (e.g. heart surveillance and breath monitoring) even on several individuals (target objects) if the required configuration of specific sensors or actuators by the concurrently operating applications is the same.

In one embodiment, the multi-application-transceiver device may be integrated in a mobile communication device, such as a smartphone or a tablet computer. The mobile communication device has IO means which enable the user to interact with the multi-application-transceiver device and optionally also with the one or more remote computers. Further, some hardware of the mobile communication device may be configured to implement hardware components of the multi-application-transceiver device (e.g., the digital signal processor component and the middleware component of the multi-application-transceiver device). This allows reducing redundancy of hardware components and, therefore, the overall complexity of the combined device and its energy consumption.

The multi-application-transceiver device communicates through its middleware with one or more remote computers. Typically such a scenario is described as a Cloud scenario where the one or more remote computers are located in the so-called Cloud and can be accessed through appropriate communication protocols (e.g., Internet protocol, GSM standard protocol, etc.). The one or more computers also referred to as Cloud computer in the following, can remotely control the multi-application transceiver device.

The Cloud computer has a data storage component to store a plurality of rule engine control rule sets. Each rule engine control rule set defines an application specific setting for one or more imaging signal transceivers and the digital signal processor component of the remote multi-application transceiver device. Each rule engine control rule set is configured to enable a monitoring application at the multi-application transceiver device. A particular rule engine control rule set can be sent to the rule engine of the multi-application transceiver device through an interface component of the Cloud computer to enable a particular monitoring application at the multi-application transceiver device. Thus, the Cloud computer decides which monitoring application is to be executed by the application agnostic transceiver device. Actually, the transceiver's multi-application capability is based on the alterable rule engine which can be remotely controlled and configured by the Cloud computer to determine the application mode of the multi-application transceiver device.

The Cloud computer can further receive through its interface component the pre-processed signal data from the multi-application transceiver device. The received pre-processed signal data is associated with the particular monitoring application which was enabled through sending the respective rule set. A data processing component of the Cloud computer can use an application specific set of services to complete processing of the received pre-processed signal data by applying application specific services to the pre-processed signal data for obtaining application specific results in the context of the particular monitoring application. In other words, complex analysis like statistical evaluation of the received pre-processed data over a longer period can be performed by using the computing resources of the Cloud computer(s) whereas computationally less complex and less expensive emergency rule evaluation can be performed onboard of the multi-application transceiver device. The results of the Cloud computer analysis may then be communicated to a client device of the user who is in control of the respective multi-application transceiver device.

The one or more Cloud computers may be used to control multiple remote multi-application transceiver devices. By controlling a plurality of such multi-application transceiver device measurement data in relation to the same monitoring application but in relation to different target objects can be collected. Therefore, the Cloud computer can compute application specific results based on the pre-processed signal data of all remote multi-application transceiver devices performing the same monitoring application to improve the reliability of the analysis results. With such data consolidation capability with regards to multiple target objects the statistical reliability of the analysis results may be improved which again can be to the benefit of each individual user of any remote multi-application transceiver device. The one or more Cloud computers may be used to generate cross application synergies. By operating a plurality of software programs at the same time and on various sensor devices, the one or more Cloud computers can integrate the data of both To summarize, the multi-application-transceiver device can communicate with at least one remote computer for delegating compute and storage tasks and for receiving control data and/or analysis data. The multi-application-transceiver device can further be communicatively coupled with one or more clients providing a graphical user interface to a user of the multi-application-sensor device. Any appropriate communication standard may be used for coupling the multi-application transceiver with the client. For example, WLAN connection or cellular communication (e.g., any GSM standard based communication), or any other appropriate communication standard may be used. The multi-application-transceiver device may also be partially or fully integrated with the client. in this case the client can share some of its hardware with the multi-application-transceiver for performing functions associated with the multi-sensor functions.

In further embodiments, a computer program product when loaded into a memory of the computer system and executed by at least one processor of the computer system causes the computer system to execute the steps of a respective computer implemented method for performing the above described functions of the computer system.

Further aspects of the invention will be realized and attained by means of the elements and combinations particularly depicted in the appended claims. It is to be understood that both, the foregoing general description and the following detailed description are exemplary and explanatory only and are not restrictive of the invention as described.

DETAILED DESCRIPTION

Figure 1:
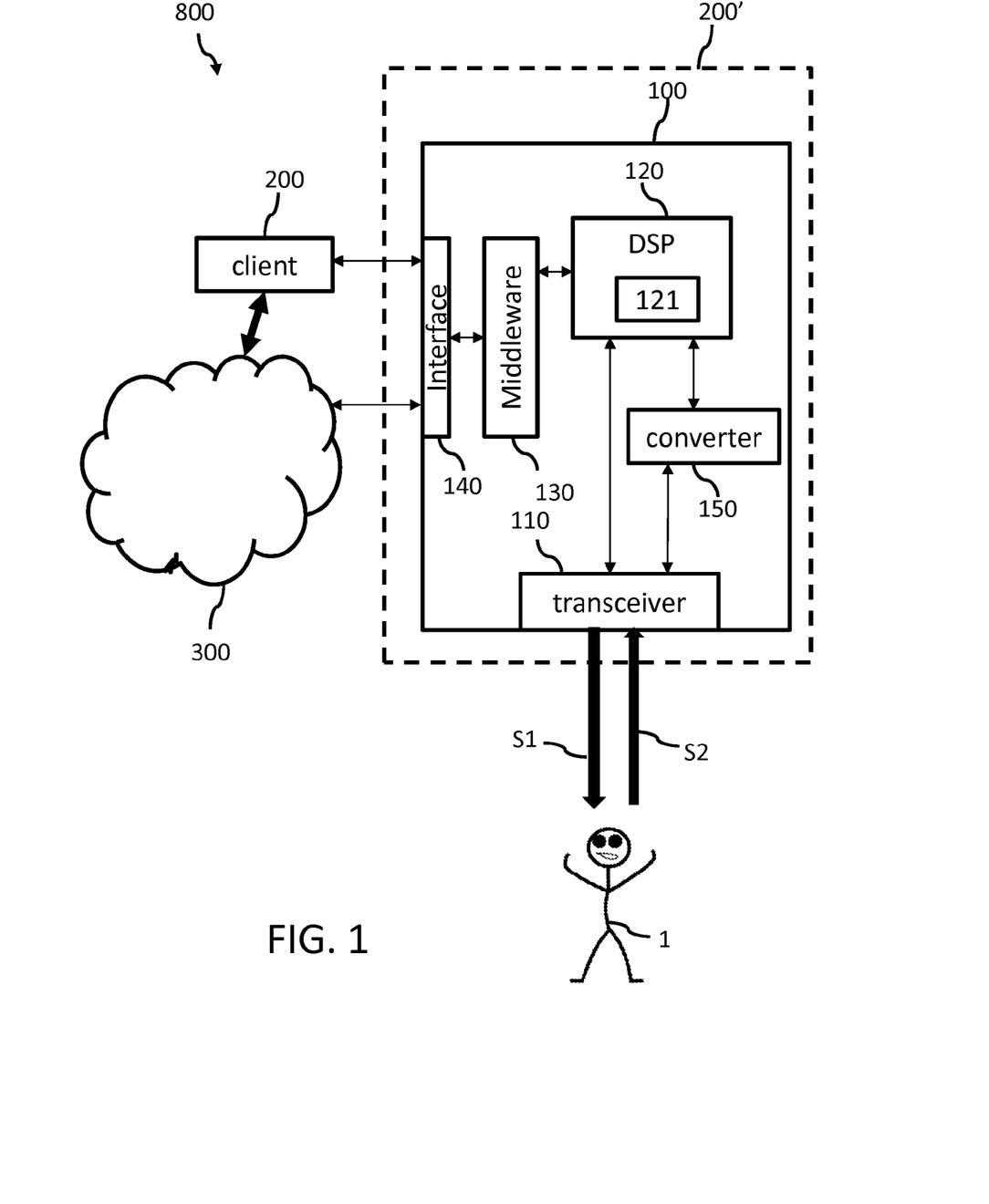
FIG. 1 is a simplified block diagram of a computer system with a multi-application transceiver device according to an embodiment of the invention.

FIG. 1 shows a simplified block diagram of a computer system 800 for target monitoring. The computer system includes a multi-application-transceiver device 100 which has at least one signal transceiver 110 for receiving a reflected signal S2 in response to an original signal S1 sent by the at least one signal transceiver 110. The reflected signal S2 is reflected from at least one target object 1. Typically such signal transceivers may be implemented through imaging sensors such as radar sensors, sonar sensors, LIDAR sensors (Light Detection and Ranging), and infrared sensors. The multi-application-transceiver device 100 may include one or more of such imaging sensors of the same type of different types. The target object may be a moving target, such as for example, one or more human beings, animals, robots, or the like. Moving in this context also includes relatively small movements, such as for example, movements of a person's chest while breathing or movements caused by a person's heartbeat. Target moving is differentiated from the non-moving environment (or static environment), depending on the application, the target can also be a part of an object or person. For example, an application monitors life activities of a sleeping person: the chest is moving, while other parts are not moving. In this example, the chest would be the target. In another example, the application detects the change of a cross-section of a birth mark, indicating its potential cancerous change (e.g., a melanoma).

The reflected signal S2 is converted into digital format by a respective converter unit 150. The converted digital signal can then be pre-processed by a digital signal processor component 120. The pre-processing of the digital signal is performed in the context of a particular monitoring application (e.g., monitoring heartbeat of target). An alterable rule engine 121 of the DSP component 120 can store a rule set which implements the particular monitoring application to discriminate a movement of the at least one target object 1 against the static environment around the at least one target object. That is, the alterable rule engine 121 can be configured to implement different monitoring applications by loading different application specific rule sets. Therefore, the multi-application-transceiver device 100 can be seen as application agnostic because dependent on the loaded rule set it may perform any monitoring application which can be based on the reflected signal data S2.

The various application specific rule sets can be received by the multi-application-transceiver device 100 through a middleware component 130. The middleware component 130 is communicatively coupled (through interface 140) with at least one remote computing device 300. The coupling may be implemented by any appropriate network technology with a respective communication protocol or a combination thereof. Examples are: TCP/IP protocols like IPv6, or others, the General Inter-ORB, Protocol (GIOP), proprietary protocols like MICROSOFT's Distributed Component Object Model (DCOM), cellular protocols like UMTS, GPRS, CDMA or others, LAN protocols like Frame Relay, Packet Radio Network Protocols like DARPA PRNET and others, Ad Hoc and Sensor Network protocols like MANET or general protocols as for example ATM, and more. The list of examples is not meant to be exhaustive. Rather any other appropriate protocol for network communication may be used instead.

The middleware component 130 can receive the rule set(s) for the alterable rule engine 121 from the at least one remote computing device 300 (e.g., one or more Cloud computers). Thereby, a received rule set defines the application specific setting for the at least one signal transceiver 110 and for the digital signal processor component 120 to enable the particular monitoring application. That is, the received rule set includes rules for the alterable rule engine to perform particular application specific actions within the transceiver device and may also include control parameters for the imaging sensor(s) 110 for optimizing the sensor capabilities for the monitoring application implemented by the received rule set. Further, the middleware component 130 sends the pre-processed signal to the remote computing device 300 where it can be further evaluated and analyzed.

The multi-application-transceiver device 100 may be communicatively coupled (e.g., via Bluetooth, WLAN, GSM, or any other appropriate communication technology) with a client device 200 which may be used by a user as a frontend to monitor and configure the multi-application-transceiver device 100. The client 200 has JO means (e.g., keyboard, mouse, touch display, screen, etc.) enabling the user to interact with the multi-application-transceiver device 100. For example, a user can query the current state of the running monitoring application or retrieve certain results which may be provided by executing the rules based on the pre-processed data. The client may also be used to select a certain notification mode for the multi-application-transceiver device 100. For example, the user may select if a notification in case of a particular event should occur via a LED signal, a beeper, a hooter, a message to the client, or any other appropriate actuator supported by the multi-application-transceiver device 100. For example, the actuator can provide an acoustic alarm or wake-up sound by the hooter.

In one embodiment, the client 200' and the multi-application-transceiver device 100 can be integrated in a single device. For example, such a device may be a mobile communication device 200' sharing some of its hardware with the multi-application-transceiver device 100 as appropriate. For example, the client 200' may provide hardware resources for implementing the digital signal processor component 120 and the middleware component 130 of the multi-application-transceiver device 100.

The application agnostic behavior of the multi-application-transceiver device 100 is based on the alterable rule engine 121, which receives its application specific rule sets from one or more computers 300 (Cloud) which are configured to control the remote multi-application transceiver device 100 accordingly. The Cloud 300 has at least one data storage component to store a plurality of rule engine control rule sets. Each rule engine control rule set defines an application specific setting for one or more imaging signal transceivers 110 and the respective digital signal processor component 120 of the remote multi-application transceiver device(s) 100. That is, the Cloud 300 can remotely configure an arbitrary number of multi-application-transceiver devices to perform a particular monitoring application by simply transmitting the respective rule engine control rule sets to the multi-application transceiver devices. This allows defining various application specific rule sets at a central location (Cloud 300) and deploying such rule sets in a flexible way to a large number of multi-application transceiver devices. Application specific rule sets may be provided from different sources or vendors in the Cloud which can all benefit from a central Cloud infrastructure to easily deploy the rules to the respective transceiver devices. Further, updates for a monitoring application can easily be deployed to the application agnostic transceiver devices by simply updating the respective application specific rule set in the Cloud 300 and re-deploying the updated application specific rule set to the transceiver devices.

Further, the Cloud 300 includes at least one data processing component which uses an application specific set of services to complete processing of the pre-processed signal data received from the multi-application transceiver device (s). The application specific services are applied to the pre-processed signal data for obtaining application specific results in the context of the particular monitoring application. In case of multiple multi-application transceiver devices connected with the Cloud 300, the quality and reliability of the analysis results may be enhanced.

The client 200, 200' is also communicatively coupled to the Cloud 300. Therefore, the Cloud 300 can communicate the results of the analysis of the received pre-processed data to the client 200, 200'. On the other hand, the client 200, 200' can access the Cloud to change the configuration of the application specific services or the application specific rule sets of to query particular analysis results not being sent automatically to the client.

Figure 2:
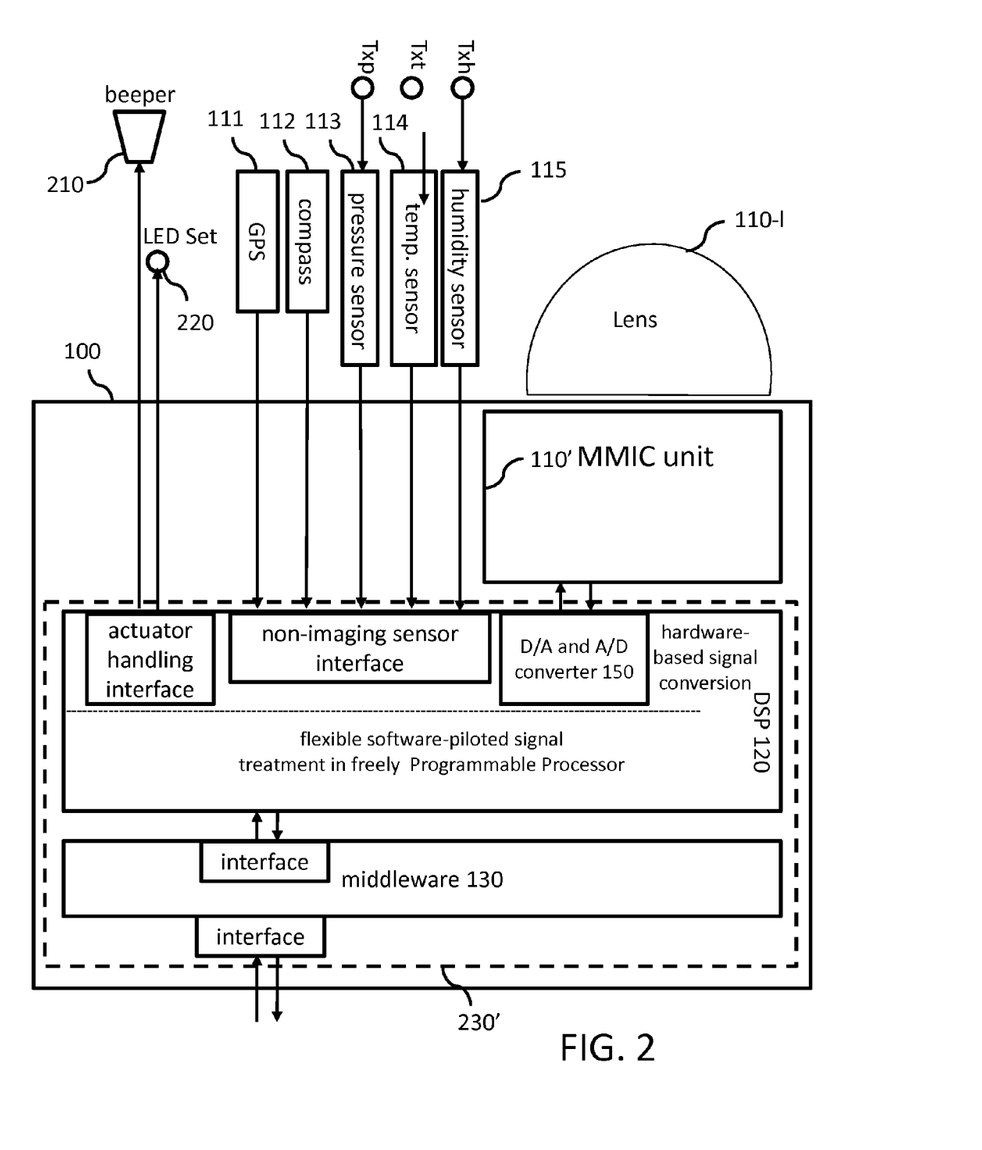
FIG. 2 illustrates components of the multi-application transceiver device according to an embodiment of the invention.

FIG. 2 illustrates components of the multi-application transceiver device 100 according to an embodiment of the invention. The components of the multi-application transceiver device 100 are exemplary only and may be implemented by a person skilled in the art by using a different cut in functionally. That is, certain functions of a particular component may also be implemented by other components which may require a different setup compared to the shown architecture also regarding the interfaces. For example, the DSP unit 120 may be implemented as a single board computer (SBC) component. A single-board computer is a complete computer built on a single circuit board, with microprocessor(s), memory, input/output (I/O) and other features required of a functional computer.

The multi-application transceiver device 100 includes a Monolithic Microwave Integrated Circuit (MMIC) unit 110' which operates the imaging sensors. The MMIC 110' may operate one or more radar, sonar, lidar and/or infrared units (single, common or redundant operation). The MMIC unit 110' can be protected by the lens 110-1. For example, the lens can protect the sensors from mechanical damage, dust or humidity but does not restrain the sensors' functionality. The reflected signals received by the imaging sensor(s) are converted to digital format by the converter 150. The converter 150 may be a part of the DSP unit 121 or a separate component (cf. FIG. 1) or even be an integrated component of the MMIC unit 110'.

In general, the DSP 120 has a hardware layer for implementing the interfaces to various sub-components and for the signal conversion and further has a software layer for flexible software-piloted signal treatment in a freely programmable processor. The freely programmable processor may be implemented by a Field Programmable Gate Array (FPGA) but may also include more intelligent processors being able to process higher languages, such as for example Node.js or Julia. The hardware layer may include an actuator handling interface to control actuators such as the beeper 210 or one or more light emitting diodes (LED Set) 220. It may further include an interface for communicating with non-imaging sensors, such as a global positioning system (GPS) sensor 111, a compass sensor 112, a pressure sensor 113, a temperature sensor 114, and a humidity sensor 115.

All the non-imaging sensors are optional and may provide additional information to improve the information transported by the reflected signal from the imaging sensor(s) in a particular monitoring application context. The converters 150 provide digital I and Q data to the DSP based on the reflected signal data received by the imaging sensors of the MMIC unit 110'.

The SW layer of the DSP unit 120 can pre-process all the received information with its flexible software-piloted signal treatment. The SW layer may perform some signal processing on board with the freely programmable processor which may result in control signals for the actuators 210, 220.

The middleware 130 is interfaced with the DSP 120 and the Cloud computer to forward the pre-processed signal to the Cloud for further processing and to receive the application specific rule sets from the Cloud. The middleware 130 may also be interfaced with the client in the case of a remote client (cf. FIG. 1, client 200). In the case where the multi-application transceiver device 100 is integrated in a mobile computing device which can play the role of the client 200' (cf. FIG. 1) the components which are grouped by the dashed frame 230' are components which can potentially be provided by the hardware resources of the client 200'. The middleware 130 in general relates to software that enables communication and management of data in distributed applications. The middleware 130 can communicate, for example, via WLAN-Rooter-Internet or through cellular communication systems with the Cloud Server and via WLAN or cellular systems with clients (e.g., smart phones) of connected users. Communication with the latter can serve for security features and makes the system failsafe. For example, it may communicate alarms and basic but important analysis features (e.g., child is breathing) even when an Internet connection is not available. As stated above, in an integrated structure, the system can use the middleware of the client.

Figure 3:
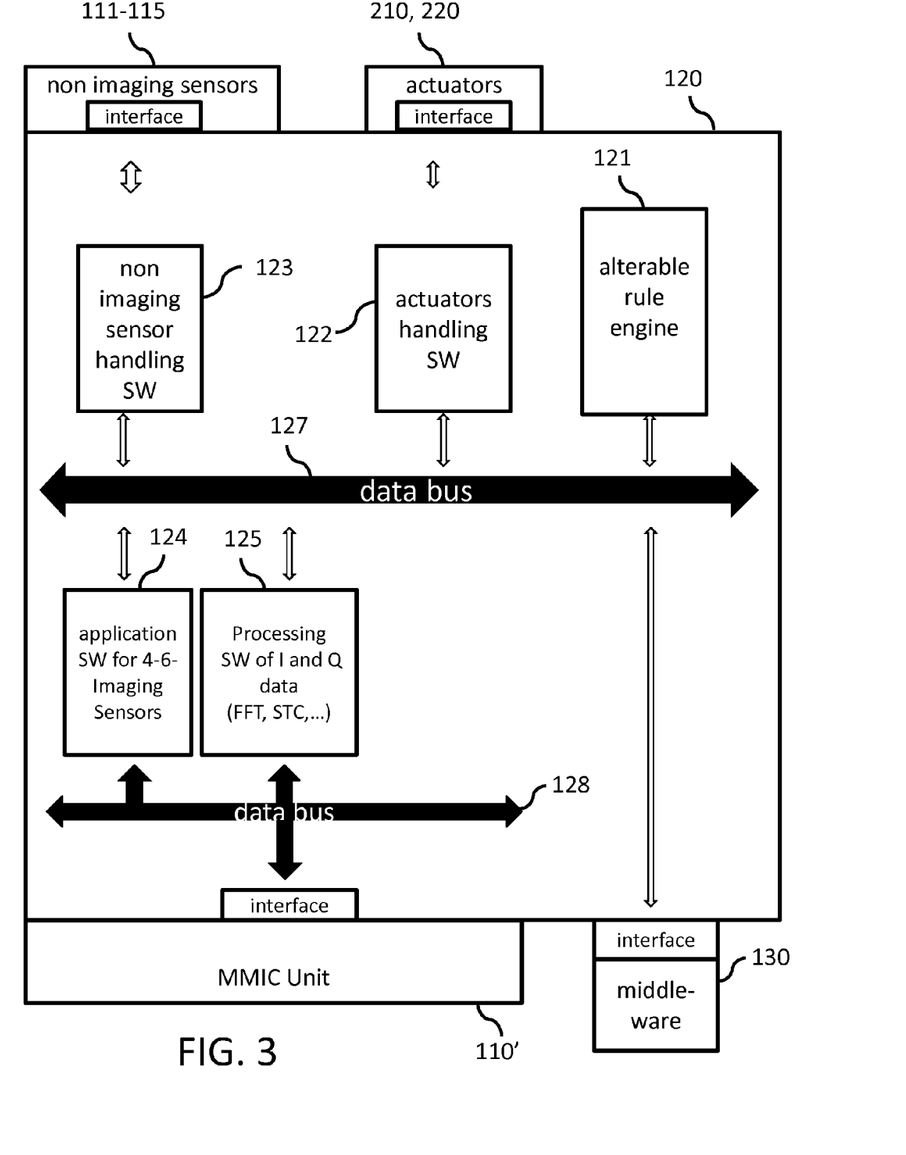
FIG. 3 shows a functional view of a DSP unit of the multi-application transceiver device according to an embodiment of the invention.

FIG. 3 shows a functional view of the DSP unit 120 according to an embodiment of the invention. FIG. 3 will be explained in the context of a monitoring application to detect the sudden Infant Death Syndrome (SIDS) and/or for the supervision of babies with congenital heart defects. The following scenario is exemplary only and intended to explain the functioning of the application agnostic sensor. It is not intended to limit the scope of the claims in any way to the described example. The person skilled in the art can implement other monitoring applications by applying the disclosed concepts to other use cases. The DSP unit 120 has a first data bus 127 for enabling the communication amongst the various SW components 121 to 125 of the DSP and the middleware component 130. It further has a second data bus 128 for communication of the SW components 124, 125 with the MMIC unit 110'. The second data bus 128 may also be connected with the middleware 130.

Example 1: Sudden Infant Death Syndrome and/or to Monitor the Baby in Cases of Congenital Heart Defects For example, a user may select an application on his client device (e.g. a native application on a mobile phone) to monitor his baby for protection against Sudden Infant Death Syndrome and/or to monitor the baby in cases of congenital heart defects. This selection of a particular monitoring application is sent to the Cloud computer(s) 300 (cf. FIG. 1) where it initiates the rule engine control services unit 310 of the Cloud computer(s) 300 (cf. FIG. 5) to send the respective application specific rule set to the alterable rule engine 121 of the corresponding multi-application transceiver device 100. For example, the rule set can be formulated and transported in a JavaScript Object Notation (JSON)-based message. The rule set may include three main blocks.

Block A of the rule set may contain the general configuration parameters for the sensors and actuators. Block B may describe the handling parameters for signal processing in the DSP unit 120. Block C may contain the execution rules, e.g., formulated as Event Condition Action (ECA) rules. The following pseudo-code lines describe an extract of code for block A. The code is structured in one object per sensor of unordered, comma-separated key-value pairs. The value can be a number, a string, a Boolean, an array, or null. When not activating a sensor or an actuator, the pseudo-code uses the Boolean value "false" in the curly braces of the corresponding object.

Pseudo-Code Example Block A:

```
applicationSoftwareRuleSet{
    radarUnit{
        range: [2000, 6000];
        frequency.EmitterSignal : 23800;
        amplification.EmitterSignal: 20
        angle.PhasedArray.EmitterSignal: 15;
        operateMode.EmitterSignal: CW;
        scanMode: Common;
        . . .
    }
    SonarUnit{
        range: [2000, 6000];
        bitRate: 4;
        scanMode: Common;
        operateMode.Emitter: Pulse;
        . . .
    }
    Infrared{false};
    humiditySensor{false};
    temperatureSensor{false};
    pressureSensor{false};
    compass{true};
    gps{false};
    led{true};
    beeper{true};
    . . .
```

The above pseudo-code depicts a small fraction of the basic configuration parameters, which are provided by the rule engine 121 to the components actuators handling SW 122, non-imaging sensor handling SW 123 and application SW 124. These parameters define for example the distance range (between device and target) which is monitored by the radar sensor as an array with the minimum range 2000 mm and the maximum range 6000 mm. It further sets the carrier frequency of the emitted signal at 23800 MHz. It also defines the amplification of the signal as 20 dB, the electronically generated angle of the phased array antenna as 15°, and the operation mode as constant wave. The scan-Mode is set to common, meaning it provides signals that can be used for Synthetic Aperture Radar analysis. The pseudo-code also provides exemplary parameters for the sonar sources and switches several sensors off (e.g., infrared, humidity sensor, temperature sensor).

The task of block B is the provision of processing parameters. It describes the concatenation of steps and the parameters used in each step. It starts with a Fast Fourier Transform (FFT), sets the sensitive time control STC (first parameter zero means no blinded out area around the source; it filters through a square root function), then operates Multi-Target Detection (MTD), etc. The pseudo-code also sets an exemplary specific target, the target "baby", defined through an array of longitudinal radar cross section and its dynamic Doppler behavior (Doppler set "true"). It also defines target characteristics. For example, the breathing frequency of a baby is communicated as an array describing the range of the baby's respiration per minute with minimum (10 breaths/minute) and maximum frequency (80 breaths/minute), averages over a period of 15 seconds.

Pseudo-Code Example Block B:

```
processingSoftwareRuleSet{
    radarUnit{
        fft;
        stc: [0,2];
        mtd: ( );
        rcs: ( );
        . . .
    }
    sonarUnit{
        . . .
    }
    New{
        baby.Target: [20, 50, true]
        breathingFrequency.Baby: [10, 80, 15]
        . . .
    }
```

Block C of the rule-set describes the Event Condition Action rules. It may include 3 subsets:
- an event part specifying the signal that triggers the invocation of the rule
- a condition part being a logical test that, if satisfied or evaluates to true, causes the action to be carried out
- an action part including updates or invocations on the local data The following sequence of pseudo-code describes in a simplified way the event (breathing frequency of a baby), the condition (signal below acceptable limit), and the action (alarm). For simplified visualization, the pseudo-code uses the key "logic", paired with a string that includes the corresponding if-then construct:

Pseudo-Code Example Block C:

```
escalationRoutineSIDS{
    logic: "if baby = true
    and
    if breathingFrequency.Baby <= 20
    set SIDSalarmpattern.Beeper: true"
}
```

The software, in the handling and processing components 122, 123, 124, 125 is typically not updated during normal operations. Its updates may be driven by the Cloud 300 through a specific update process which is handled by the middleware 130. The code, used in the said components can be a high-performance dynamic programming language for technical computing. Possible examples (non-exhaustive) are openCL (e.g., when working with an FPGA), Fortran, Julia, Python, R, Octave, JavaScript or Go.

The imaging sensors are specifically operated by the MMIC unit 110' (cf. FIG. 2). The MMIC may operate one or more radar, sonar and/or infrared units (single, common or redundant operation). In each case, and defined by the active rule-set, reference oscillations are conditioned into a suitable output signal (e.g., set through radarUnit{ . . . } object).

In the described SIDS case the radar transceiver is the primary sensor for the monitoring application. Through four or more independent phased array antennae it can send out low power electromagnetic beams. It scans the reflection and communicates the scanned signals via an interface to the Freely Programmable Processor. The data bus 128 transports the signals to the Processing Software 125. The above pseudo-code activates and parameterizes the applicable methods (or functions or procedures) in the Processing Software. In the given example, the processing software is set to enhance I (In-phase) and Q (Quadrature) data through Fast Fourier Transform Algorithms (FFT) and Phase-shift detection. Alternatively, this may be implemented through phasing analysis. In other words, various methods may be concatenated to process, fragment, filter, etc. the signals. Examples are Fast Fourier Transform (FTT), Analysis of Phasing and Sensitive Time Constant (STC), and Video Pulse Train. Through the processing software, configured by the rules of block B, the radar transceiver can detect individual humans in a room (Moving Target Detection MTD). Through radar cross section analysis it can discover the baby among the humans and indicate the baby. The compass sensor allows determining positioning of the baby relative to its parents. The unit also can recognize when the baby leaves the room (baby=false). In that case, the escalation routine "SIDS" will not set off, although the radar does not recognize any breathing. With prior art sensor devices, this may lead to problems, as the device needs to be switched off when the baby leaves the room. Embodiments of the invention use signals coming from a set of phased array antennae and the processing software is able to apply synthetic aperture radar algorithms, e.g., the range-Doppler algorithm or the chirp-scaling algorithm, to create a resulting image of higher resolution or of 3D nature. The output of the processing component 125 is the pre-processed signal which can be sent by the middleware component 130 to the Cloud computer 300. A subsequent signal enhancement step allows enhancing the received data through time-frequency analysis of Doppler patterns. In contrast to prior art sensors, the proposed transceiver device can alternatively operate on the basis of Synthetic Aperture Sonar. It can thus completely operate without on electro-magnetic non-ionizing radiation and completely rule-out radiation-related health impacts. Alternatively to the active radar as disclosed in the example scenario, the invention may be operated using a passive radar. This alternative approach uses the reflection of existing non-ionizing electro-magnetic radiation of external origin (e.g. from Wireless LANs or Mobile Phones). As a consequence, it does not add any electro-magnetic radiation at all.

The middleware component 130 communicates the pre-processed signal to the Cloud computer 300 (cf. FIG. 1) for subsequent analysis. For example, it can use web-socket based communication, allowing for streams of messages over the TCP protocol through dedicated ports. Alternatively, RESTful messages can be sent. In that case, each message is autonomous and needs to carry all identifying information in the header.

Figure 5:
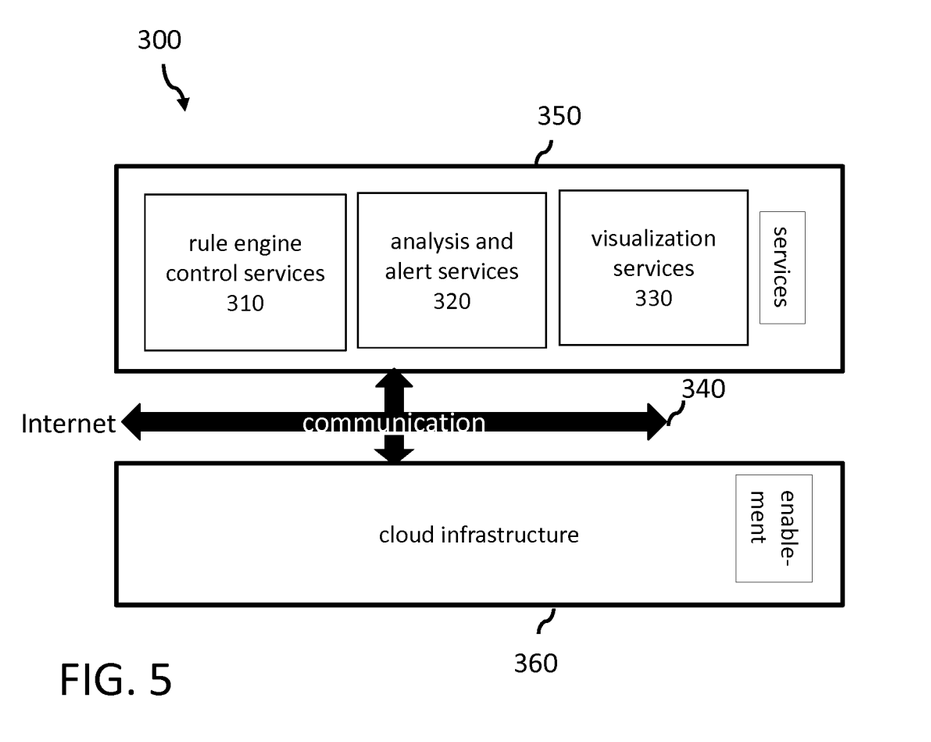
FIG. 5 is a component view of at least one remote computer for controlling the multi-application transceiver device according to an embodiment of the invention.

FIG. 5 shows details the one or more (Cloud) computer(s) 300 for controlling the application agnostic multi-application transceiver device(s). The computer 300 is also referred to as server hereinafter. The server has a Cloud infrastructure 360 which can provide basic Cloud functions. For example, on the server, the flow and exchange of data can be organized through message queues. Following the concept of service oriented architecture (SOA), each discrete piece of self-contained software provides application functionality as services to other applications. The services can be loosely coupled to composite services, able to provide more complex functionality.

The above described example analysis and alert services 320 can analyze heart and breathe functions. They can operate in two different modes: Firstly, they can monitor the functions at a specific moment in time. If breath stops, they may send visual and/or acoustic alarm to the client. In parallel, the Event Condition Action (ECA) Rules on the transceiver device are able to activate the acoustic alarm in the sensor device, for example, to wake up the baby and thus to reactivate its breath. The multi-application transceiver device is enabled to send a visual and/or audio emergency signal to defined client devices, based on the ECA rules. Those alarm signals can alarm parents or a babysitter to incite immediate action.

Beyond the above described real-time oriented monitoring, Cloud analysis and alert services 320 can also do long time analysis. They can produce reports, based on data analysis over longer periods, e.g., over one month as well as evaluation of data collected from multiple multi-application transceiver devices. Comparison with data from the same or similar applications performed on different multi-application transceiver devices provides a basis for data mining and comparative analysis and hence for more extensive and early detection screening. Anonymized data may for example be shared with universities in real-time to support scientific research. The visualization services 330 provide means to communicate 340 and display the analysis results on the client devices 200, 200' (cf. FIG. 1). The communication 340 between the Cloud 300 and the client devices 200, 200' can be accomplished e.g., in a RESTful way: for example, JSON-based messages that were conditioned by visualization services 330 can be sent to native Apps, which visualize them on mobile phones.

The graphical visualization services may help creating graphical visualization of objects, parameters and environment, building on the data from the abstract visualization language. Depending on the nature of the client, the service may either be fully operated in the Cloud, or may operate as application on the client (e.g., Smart Phone). In the latter case the Cloud service only may provide symbols and a correlation list of identifier class and symbol. Provision in this case may occur either just in time or asynchronously, e.g., in the frame of regular updates. The correlation list of identifier class and symbol evolves over time Graphical visualization may occur as follows: each identifier class of objects or environment has a corresponding symbol (e.g. a baby is depicted with a baby symbol). A visual language gives guidance through producing the right information in the right moment through its context specific representation of symbols, reinforced by the blinding out or deactivation of unsuitable properties. As a consequence, the user receives customized information for each specific modeling step. Simplified visualization and selective omission of data allows the creation of an enhanced overview perspective. Data which does not contribute value in the context of the application may be omitted. The language may also apply visual stimulus (e.g., in specifically depicting heartbeat). Different graphical visualization allows focusing on different application targets (e.g., when showing that a heartbeat is ok, a beating heart may be depicted in green. When giving an analysis, heart data may be provided as static curves and figures). Parameters like object speed can be visualized in an additional dimension (pop-up box) through clicking on the object. As a consequence, communicated parameters can be visualized and allocated on graphical displays, despite of reduced bandwidth. The amount of visualized data can be defined in the settings of the native application on the client device. Depending on the user's preferences, the visualization can thus be customized.

Embodiments of the invention may outperform prior art solutions through several means. Here are some examples: prior art sensors for Sudden Infant Death Syndrome may only be able to measure when the baby is placed alone in its bed. The above disclosed approach allows the baby to sleep next to its parents without reducing the capability to detect breath or heartbeat interruptions. It further detects when the baby leaves the room and does not send false alarms in these cases. The 3D analysis further allows measuring the position of the baby, thus the risk of suffocation through pressing the nose into a pillow is drastically reduced. Early detection of malfunctions can be generated through long time screening, as compared to prior art sensors, data storage capacity is not limited in the Cloud. The analysis of comparative big data allows for an early detection of off-the-norm breathe or heartbeat behavior. The provision of big data may support advancing state of the art in medical research. An additional provision of application rule sets on adult sleep apnea or cardiac dysrhythmia allows monitoring of the parents at the same time.

Analysis and support services 320 may include services which allow for a plurality of analyses, also through connections or mash ups with external services or internal/external data mining. Analysis services can build on other analysis services (composite nature) and may be of third party origin. Examples of analysis services are:
- Monitoring movements, breath, heartbeat of human beings, providing analysis, sending alerts.
- Intrusion detection (Perimeter surveillance) and accident prevention (e.g., pool surveillance to avoid children's accidents).
- Professional services (prison cell surveillance, customs control, hospitals, old people's hostels, etc.).
- Cardiac dysrhythmia supervision with analysis reports and alarms.
- Sleep apnea supervision with analysis reports and alarms.
- Instant Child Death prevention and alarms.
- Baby asphyxia (death by asphyxiation through face downsided into the pillow).
- Scan several persons concurrently through (Moving target indication).
- Gym, supervising people who are overdoing.
- In hospitals, concurrent scanning could be possible.
- In the hospital waiting room: detect people, who need immediate care.
- Prisons: to check whether prisoners are still there, to avoid suicides etc.
- Borders: find out potential smugglers/terrorists (acc. heartbeat/breath).

For example, the monitoring application may be configured to discover the presence of and to estimate the concentration of specific macromolecules (e.g., the protein p53 or p53 antibodies) in a sample target object (e.g., exhaled fluid on the lens) through the magnitude of re-emitted electromagnetic radiation having a frequency within the specific resonance frequency range of the macromolecule. Detecting the protein p53 or its antibodies through analysis of the re-emitted electromagnetic radiation from the fluid, exhaled on the device's lens may be an indicator for cancer because p53 is in specific concentrations and conditions an indicator for cancer.

A person skilled in the art can apply the above disclosure to implement embodiments of the invention directed to other monitoring application scenarios as briefly disclosed in the following.

Example 2: Melanoma Detection

With a different application specific rule set, human skin can be analyzed for melanoma. For example, in a bathroom, a radar sensor can detect persons. The rule-set in the alterable rule engine 121 (cf. FIG. 3) may be conceived accordingly by the rule engine control services 310 (cf. FIG. 5). Paired with suitably conceived analysis and alert services 320, the application agnostic transceiver device becomes part of a significantly different monitoring, analysis and alert application. The generic process of rule provision, sensing, analysis and communication between sensor device, Cloud and client remain the same as in example 1 described earlier. A sonar sensor of the multi-application transceiver device can scan the skin of an undressed human via a 3D synthetic aperture sonar approach (using a Synthetic Aperture Sonar algorithm). Receiving the pre-processed data, the Cloud based services can do long term supervision and analysis for a detection of malignant tumors. This example application scenario particularly benefits from the interplay of several image giving sensors: The radar sensor serves to detect the moving target (MTD) and to indicate the detected target (based on cross section and size) as a specific person in the household (e.g., to differentiate a baby from its parents). The sonar sensor in FIG. 4 performs the skin scanning. In this example, the state in change of the person with regards to the sonar signal may be caused by a cross-section change of the person's melanoma under the skin.

Figure 4:
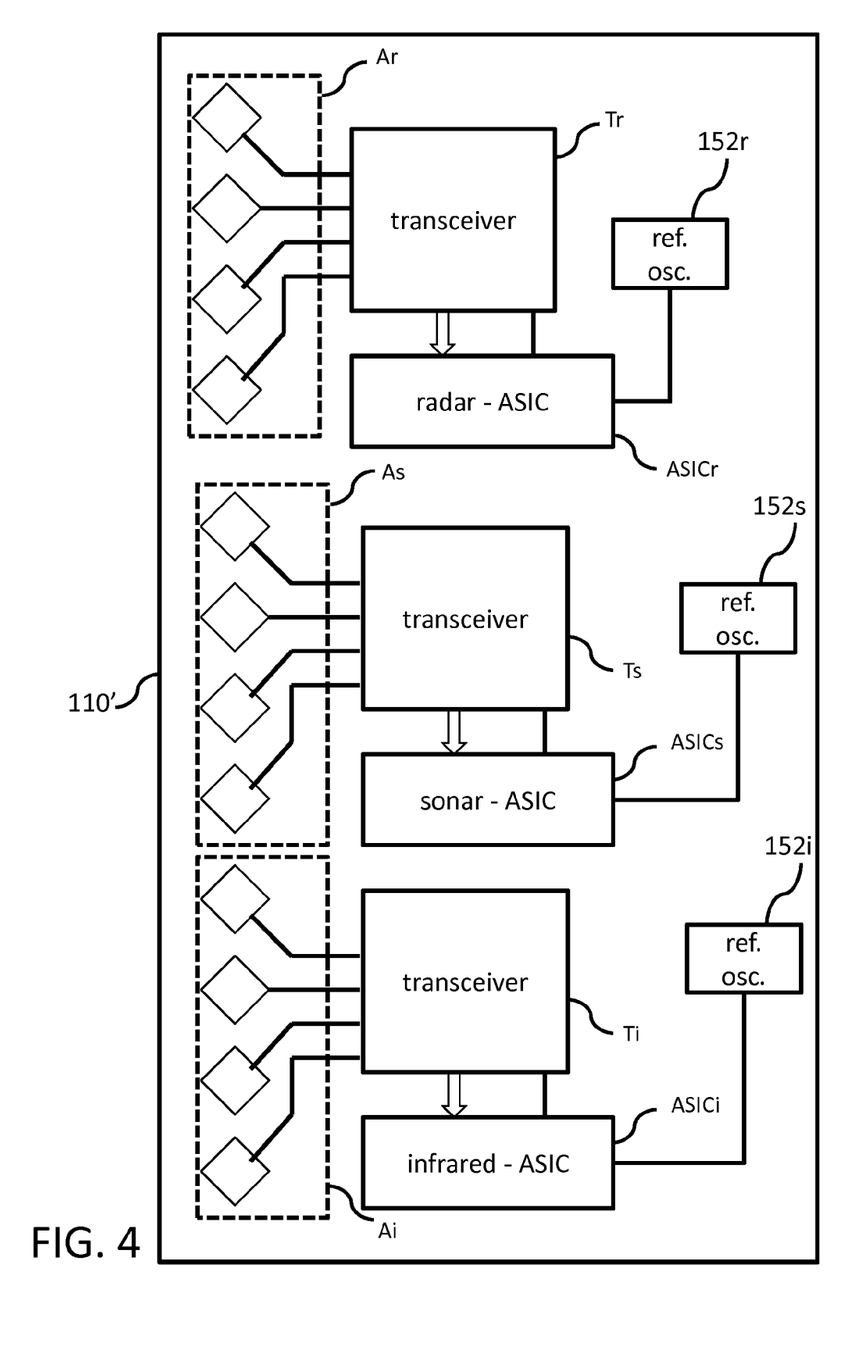
FIG. 4 illustrates a multi-transceiver set up according to an embodiment of the invention.

Monitoring applications like the above using multiple transceiver/sensor types can use a multi-transceiver setup of the MMIC unit 110' as exemplary illustrated in FIG. 4. For example, a Silicon-Germanium-based Monolithic microwave integrated circuit may be used in the MMIC unit 110' for implementing a plurality of transceivers Tr, TS, Ti of different types (e.g., transceivers operating at different wavelengths and media like radar, sonar, infrared, etc.). The MMIC can use a respective reference oscillator source 152r, 152s, 152i for each transceiver, whose frequency is conditioned by application specific integrated circuits (ASICr, ASICs, ASICi). There can be separate oscillators for radar application, sonar application and infrared application, respectively. The radar transceiver Tr provides the signals to 4-6 phased array antennae Ar, which send the signal S1 (cf. FIG. 1) to the target object which receive the reflected radar signal S2. The 4-6 phased array antennae supply several sets of radar data (equal to the number of antenna). The other transceivers Ts, Ti use similar phased array antennae setups As, Ai. Such sets of spatially offset antennae can help to create abstract radar images taken from spatially shifted perspectives during the subsequent data enhancement in the DSP. This spatial shift is, in particular, is the basis for the subsequent synthetic aperture radar processing. The MMIC may also include the converters 150 (cf. FIG. 2) for D/A and A/D conversion with a fast sampling rate to deliver digital I/Q data to the DSP. D/A and A/D converters 150 already integrated into the MMIC unit allow for a direct coupling with clients (e.g. with smartphones), without a requirement to modify the hardware of the client. The data can pass existing digital signal interfaces on the client circuit board which leads to a reduction of complexity in the manufacturing and integration process.

Mounting the phased array antennae Ar, As, Ai, on the MMIC in an automatic production process (when producing the MMIC) may provide several advantages: miniaturization of the unit; improved connection leading to cleaner signals which can be important in the high frequency bands of sonar and radar sensor; reduced complexity through automated and standard production and quality control process.

Example 3: Intrusion Detection

In a radar-based monitoring application, similar to example 1, but with a different rule set and placed outside a building, the transceiver device can detect intruders and define their quantity and radar cross section. In this case, the sensor may not need highest resolution but a broader angle. Hence, the scan-mode of the radar transceiver may be "single". The range can be adapted on the terrain around the building (e.g. from 10 to 30 meters, leading to a distance range parameter "range: [10000, 30000]. The monitoring application may be supported by GPS and compass sensors, which can be set "true". It may further operate in interaction with linked open geospatial data, which are received from the rule engine control services 310 in the Cloud and which are provided to the rule engine 320 to more precisely define the position of the potential intruder(s). Making use of the Doppler effect, the speed and direction of movement of the intruder(s) can be assessed. The users of the application may be alerted via the client. The analysis and alert services 320 may alert the user, and/or for example, a predefined security company. Such user-specific information can be made available to the analysis and alert services 320 through a multi-tenant design of the Cloud architecture and can be stored in a multi-tenant database in the Cloud infrastructure.

Operating several thematically separate monitoring applications in parallel enables new enhanced operations performed by the multi-application transceiver device. For example. If an intrusion into a perimeter is detected in a house of a person whose heart performance was antecedently analyzed to be instable, an algorithm can suggest suitably adapted operations (e.g., alert the professional caregiver).

Figure 6:
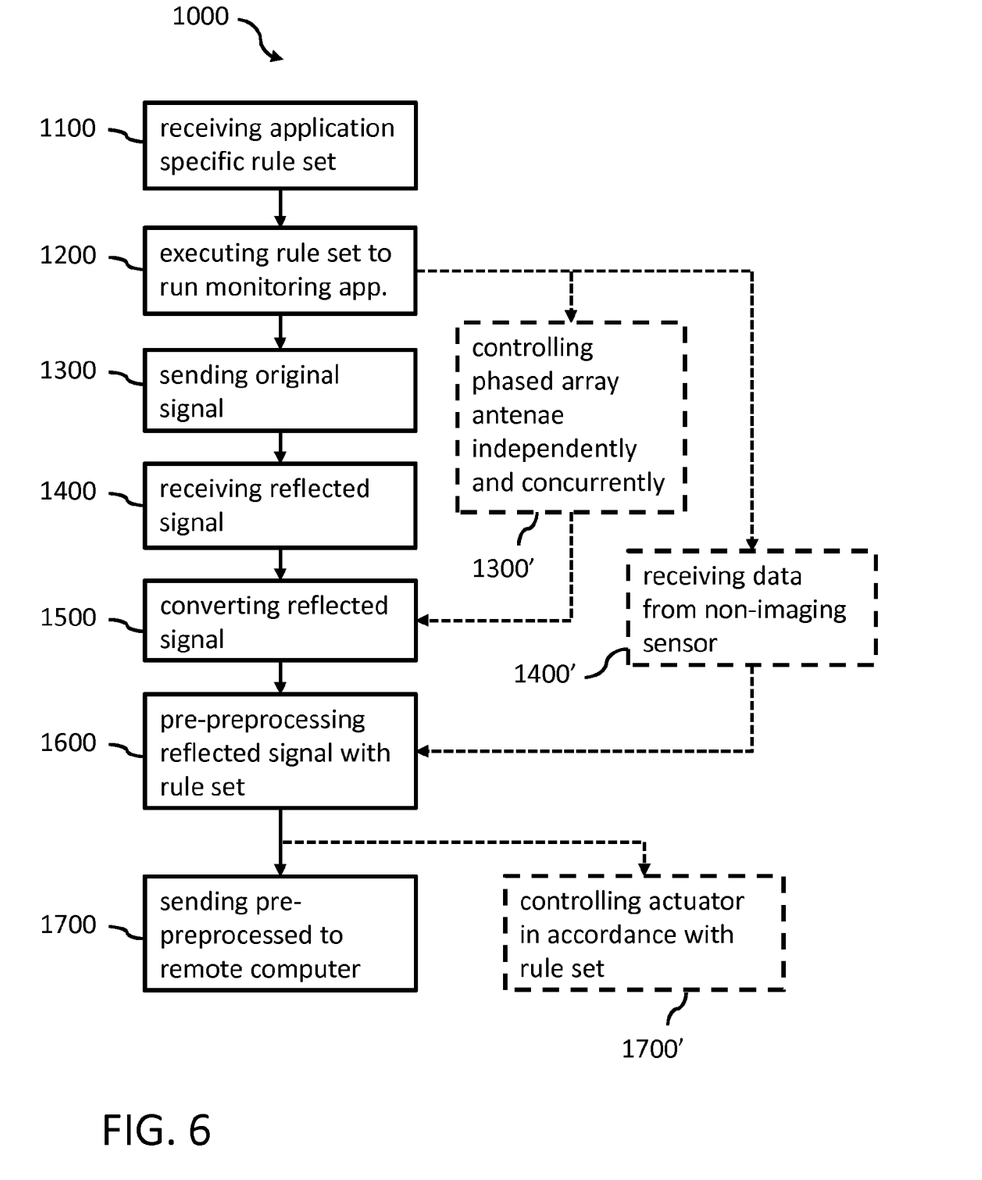
FIG. 6 is a flowchart of a computer implemented method for operating the multi-application transceiver device according to an embodiment of the invention.

FIG. 6 is a flowchart of a computer implemented method 1000 for operating the multi-application transceiver device according to an embodiment of the invention. Optional elements of the method 1000 are illustrated by dashed frames/lines. Steps are not necessarily to be executed in the order as visualized. A person skilled in the art will recognize steps which may be executed in parallel with other steps of the method 1000.

The computer implemented method 1000 starts with receiving 1100 at the multi-application transceiver device from at least one remote computer 300 an application specific rule set. The rule set may be provided by a Cloud computer as disclosed earlier and defines an monitoring application specific setup for the multi-application transceiver device. The multi-application transceiver device then executes 1200 the application specific rule set with an alterable rule engine to run the monitoring application according to the rule set. By loading different rule sets the rule engine can execute various monitoring applications. This feature makes the transceiver device application agnostic. In other words, a particular application use of the transceiver device may be remotely configured and changed by the Cloud computer through sending respective rule sets to the transceiver device. Also updates of an application can be provided this way. The transceiver device has at least one signal transceiver for sending 1300 an original signal towards at least one target object, and for receiving a reflected signal in response to the original signal. The reflected signal is thereby reflected from the at least one target object. The signals may be radar, sonar, LIDAR, and/or infrared signals.

In one embodiment, sending 1300 the original signal and receiving 1400 the reflected signal is performed with one or more phased array antennae and/or probes. Thereby, the transceiver device may control 1300' the one or more phased array antennae and/or probes independently and concurrently.

The reflected signal is converted 1500 into digital format and then pre-processed 1600 with the received rule set to discriminate a movement of the at least one target object against a static environment around the at least one target object in the context of the monitoring application.

In one embodiment, additional sensor data may be received 1400' from at least one non-imaging sensor. The non-imaging sensor(s) may be an integral part of the multi-application transceiver device or may be communicatively coupled and provide the additional sensor data via an appropriate communication protocol. The additional sensor data can then be used in the pre-processing step 1600 to compute the pre-processed signal. Enrichment of the reflected signal data with additional non-imaging sensor data can improve the accuracy of the pre-processed data and/or extend the monitoring functions of the monitoring application. For example, measuring an accelerated heartbeat of a person with a radar transceiver in combination with a temperature raise in the room where the person sleeps may indicate that the accelerated heartbeat is simply caused as a reaction to the temperature raise in the room and not to any health problems of the person.

The pre-processed signal data is then sent 1700 to the remote computing device for further processing (e.g., analysis, report generation, etc.)

In one embodiment, the multi-application-transceiver device on its own can control 1700' one or more actuators coupled with the transceiver device in accordance with the received rule set. The actuator(s) may indicate a device and/or application status. This allows the multi-application transceiver device to independently (without connection to the remote computer) react to specific events, such as for example, emergency situations. The rule set may have a basic function portfolio to analyze such events already during the pre-processing 1600 of the signal data and can trigger corresponding actuators (e.g., beeper alarm) if a particular event is detected. It may also forward the information to a client device which is coupled with the transceiver device.

A person skilled in the art will understand that the computer implemented method 1000 can be enhanced by further features disclosed in detail in the previous description of the multi-application transceiver device and the Cloud computer(s). Method steps of the invention can be performed by one or more programmable processors executing a computer program to perform functions of the invention by operating on input data and generating output. Method steps can also be performed by, and apparatus of the invention can be implemented as, special purpose logic circuitry, e.g., an FPGA (field programmable gate array) or various ASICs (application-specific integrated circuit). Processors suitable for the execution of a computer program include, by way of example, both general and special purpose microprocessors, and any one or more processors of any kind of digital computing device. Generally, a processor will receive instructions and data from a read-only memory or a random access memory or both. The essential elements of a computer are at least one processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, optical disks, adhesive tapes or other storage means. Such storage devices may also be provisioned on demand and be accessible through the Internet (Cloud Computing). Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the invention can be implemented on a computer having a display device, e.g., a cathode ray tube (CRT) or liquid crystal display (LCD) monitor, for displaying information to the user and an input device such as a keyboard, touchscreen or touchpad, a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of such back-end, middleware, or front-end components. Client computers can also be mobile devices, such as smartphones, tablet PCs or any other handheld computing device. The components of the system can be interconnected by any form or medium of digital data communication, e.g., a communication network. Examples of communication networks include a local area network (LAN) and a wide area network (WAN), e.g., the Internet or wireless LAN or telecommunication networks.

The computing system can include clients and servers. A client and server are generally remote from each other and typically interact through a communication network. The relationship of client and server arises by virtue of computer programs running on the respective computers and having a client-server relationship to each other.

What is claimed is:

1. A multi-application-transceiver device for monitoring a health of a person, comprising:
    a middleware component configured to receive a rule set, over a network, from a remote computing device storing a plurality of rule sets, each rule set corresponding to a different health monitoring application, the received rule set defining application specific settings for a first health monitoring application to be enabled on the multi-application-transceiver device, the application specific settings including sensor configuration parameters, digital signal processing parameters, and event condition action rules, which are used to implement and execute the first health monitoring application;
    a digital signal processor component having a microprocessor and memory, the digital signal processor component including an alterable rule engine configured to store the received rule set in the memory and implement the first health monitoring application by loading the application specific settings of the received rule set,
    the alterable rule engine adapted to configure sensors on the multi-application-transceiver device according to the sensor configuration parameters such that at least one sensor is configured to transmit one or more signals and receive one or more reflected signals reflected from the person in accordance with the sensor configuration parameters,
    a signal conversion unit configured to convert the reflected signals into digital format,
    the digital signal processor component configured to signal process the converted reflected signals using the digital signal processing parameters of the received rule set to detect a heartbeat frequency of the person in a context of the first health monitoring application; and
    an interface configured to communicate results of the signal processing to a user or the remote computing device according to the event condition action rules of the received rule set, the interface including an actuator configured to communicate the results to the user in accordance with the event condition action rules of the received rule set such that the multi-application-transceiver device can react to specific events independently and without connection to the remote computing device, wherein the actuator is activated when the heartbeat frequency meets an event condition of the event condition action rules,
    the middleware component is further configured to receive from the remote computing device a secondary rule set for the alterable rule engine, wherein the secondary rule set defines application specific settings for a second health monitoring application to be enabled on the multi-application-transceiver device, the second health monitoring application being a monitoring application that monitors the person or another person for a health condition that is different than the first health monitoring application,
    the digital signal processor component is further configured to signal process the received signals in accordance with the application specific settings of the first health monitoring application and in parallel with the application specific settings of the second health monitoring application.

2. The multi-application-transceiver device of claim 1, wherein the sensors include two or more sensors selected from the group of: radar sensor, sonar sensor, Light Detection and Ranging (LIDAR) sensor, and infrared sensor.

3. The multi-application-transceiver device of claim 1, wherein the second health monitoring application is configured to monitor a breathing frequency of the person.

4. The multi-application-transceiver device of claim 1, further comprising:
    a Monolithic Microwave Integrated Circuit (MMIC) unit configured to control the sensors according to the application specific settings of the received rule set of the first health monitoring application.

5. The multi-application-transceiver device of claim 1, wherein the first health monitoring application is configured to monitor for sudden Infant Death Syndrome (SIDS).

6. The multi-application-transceiver device of claim 1, wherein the sensors include a plurality of antennas, wherein the plurality of antennas are configured to be controlled independently and concurrently according to the application specific settings of the received rule set of the first health monitoring application.

7. The multi-application-transceiver device of claim 1, wherein the multi-application-transceiver device is a mobile phone.

8. The multi-application-transceiver device of claim 1, wherein the second health monitoring application is configured to discover a presence of a macromolecule in a sample of the person and to estimate a concentration of the macromolecule in the sample through magnitude of re-emitted electromagnetic radiation having a frequency within a resonance frequency range of the-macromolecule.

9. The multi-application-transceiver device of claim 1, wherein the sensors include a plurality of image sensors and at least one non-imaging sensor, and the digital signal processing component is configured to receive sensor data from the at least one non-imaging sensor, and to use the sensor data from the at least one non-imaging sensor in combination with sensor data from the plurality of image sensors when signal processing the converted reflected signals.

10. The multi-application-transceiver device of claim 1, wherein the digital signal processing component is configured to pre-process the converted reflect signals to generate a pre-processed signal, and send the pre-processed signal, over the network, to the remote computing device, the middleware component configured to receive the rule set of the first health monitoring application, over the network, from the remote computing device in response to the pre-processed signal.

11. A computer implemented method for operating a multi-application transceiver device for monitoring a health of a person, comprising:
receiving, over a network, at a multi-application transceiver device, a rule set from a remote computing device storing a plurality of rule sets, each rule set corresponding to a different health monitoring application, the received rule set defining application specific settings for a first health monitoring application to be enabled on the multi-application-transceiver device, the application specific settings including sensor configuration parameters, digital signal processing parameters, and event condition action rules, which are used to implement and execute the first health monitoring application;
implementing the first health monitoring application by loading the application specific settings of the received result set including configuring sensors using the sensor configuration parameters of the received rule set;
receiving, by at least one sensor, one or more reflected signals reflected from a target object;
signal processing the reflected signals using the digital signal processing parameters of the received result set to detect a heartbeat frequency of the person in a context of the first health monitoring application;
communicating results of the signal processing, over the network, to a user or the remote computing device for further analysis according to the event condition action rules of the received rule set, wherein the results are communicated to the user, via an actuator, in accordance with the event condition action rules of the received rule set such that the multi-application-transceiver device can react to specific events independently and without connection to the remote computing device, wherein the actuator is actuated when the heartbeat frequency meets an event condition of the event condition action rules;
receiving from the remote computing device a secondary rule set for the alterable rule engine, wherein the secondary rule set defines application specific settings for a second health monitoring application to be enabled on the multi-application-transceiver device, the second health monitoring application being a monitoring application that monitors the person or another person for a health condition that is different from the first health monitoring application; and
implementing the second health monitoring application by loading the application specific settings for the second health monitoring application such that the first health monitoring application and the second health monitoring application can be executed in parallel.

12. The computer implemented method of claim 11, wherein the sensors include a plurality of image sensors and at least one non-imaging sensor.

13. The computer implemented method of claim 12, further comprising:
receiving sensor data from the at least one non-imaging sensor, and using the sensor data from the at least one non-imaging sensor in combination with sensor data from the plurality of image sensors when signal processing the reflected signals.

14. A computer program product having executable instructions that when loaded into a non-transitory computer readable medium of a computing device and executed by at least one processor of the computing device are configured to:
receive, over a network, at a multi-application transceiver device for monitoring a health of a person, a rule set from a remote computing device storing a plurality of rule sets, each rule set corresponding to a different health monitoring application, the received rule set defining application specific settings for a first health monitoring application to be enabled on the multi-application-transceiver device, the application specific settings including sensor configuration parameters, digital signal processing parameters, and event condition action rules, which are used to implement and execute the first health monitoring application;
implement the first health monitoring application by loading the application specific settings of the received result set;
configure sensors using the sensor configuration parameters of the received rule set including setting a distance range of at least one sensor between the multi-application-transceiver device and the person;
receive, by the at least one sensor, one or more reflected signals reflected off the target object within the set distance range;
convert the reflected signals to a digital format;
signal process the converted reflected signals using the digital signal processing parameters of the received result set to detect a heartbeat frequency of the person in the context of the first health monitoring application;
communicate results of the signal processing, over the network, to a user or the remote computing device according to the event condition action rules of the rule set, wherein the results are communicated to the user, via an actuator, in accordance with the event condition action rules of the received rule set such that the multi-application-transceiver device can react to specific events independently and without connection to the remote computing device, wherein the actuator is actuated when the heartbeat frequency meets an event condition of the event condition action rules of the rule set;

receive, over the network, a secondary rule set from the remote computing device, the secondary rule set defining application specific settings for a second health monitoring application to be also enabled on the multi-application-transceiver device, the second health monitoring application being a monitoring application that monitors the person or another person for a health condition that is different from the first health monitoring application; and implement the second health monitoring application by loading the application specific settings of the secondary rule set such that the first health monitoring application and the second health monitoring application can be executed in parallel.

15. The computer program product of claim 14, wherein the executable instructions to signal process the reflected signals includes applying synthetic aperture radar algorithms to the converted reflected signals to create a resulting three-dimensional (3D) image, and the resulting 3D image is sent to the remote computing device for a time-frequency analysis.

16. The computer program product of claim 14, wherein the executable instructions include executable instructions to:

receive and implement updates for the first health monitoring application and the second health monitoring application from the remote computing device.

* * * * *